US008758992B2

(12) United States Patent
Barr et al.

(10) Patent No.: US 8,758,992 B2
(45) Date of Patent: *Jun. 24, 2014

(54) METHOD FOR THE DIFFERENTIAL DIAGNOSIS OF NON-ALCOHOLIC FATTY LIVER DISEASE BASED ON A METABOLOMIC PROFILE

(75) Inventors: Jonathan Barr, Derio-Vizcaya (ES); Azucena Castro Espido, Derio-Vizcaya (ES); Jose Maria Mato De La Paz, Derio-Vozcaya (ES); Maria Luz Martinez Chantar, Derio-Vizcaya (ES)

(73) Assignee: One Way Liver Genomics, S.L., Derio—Vizcaya (ES)

( * ) Notice: Subject to any disclaimer, the term of this patent is extended or adjusted under 35 U.S.C. 154(b) by 0 days.

This patent is subject to a terminal disclaimer.

(21) Appl. No.: 13/497,505

(22) PCT Filed: Sep. 20, 2010

(86) PCT No.: PCT/EP2010/063792
§ 371 (c)(1),
(2), (4) Date: Mar. 21, 2012

(87) PCT Pub. No.: WO2011/036117
PCT Pub. Date: Mar. 31, 2011

(65) Prior Publication Data
US 2012/0187289 A1 Jul. 26, 2012

(30) Foreign Application Priority Data

Sep. 22, 2009 (EP) .................................... 09382174

(51) Int. Cl.
*C12Q 1/00* (2006.01)
(52) U.S. Cl.
USPC .................. 435/4; 436/63; 250/281; 250/282
(58) Field of Classification Search
CPC .............. G01N 33/92; G01N 2500/00; G01N 2800/00; A61K 31/201; A61K 31/203; A61K 31/205; G06F 19/24
See application file for complete search history.

(56) References Cited

U.S. PATENT DOCUMENTS

| | | |
|---|---|---|
| 2006/0135420 A1 | 6/2006 | Mato De La Paz et al. |
| 2007/0037287 A1 | 2/2007 | Takatsuki et al. |
| 2007/0231811 A1 | 10/2007 | Mato De La Paz |
| 2009/0304704 A1 | 12/2009 | Gerhard et al. |
| 2010/0068746 A1 | 3/2010 | Nakajima et al. |
| 2011/0212468 A1 | 9/2011 | Kohli et al. |
| 2012/0187289 A1 | 7/2012 | Barr et al. |

FOREIGN PATENT DOCUMENTS

| | | | |
|---|---|---|---|
| EP | 2157431 A1 | * | 2/2010 |
| WO | 2008021192 A2 | | 2/2008 |

OTHER PUBLICATIONS

Bozovic A. et al., REVIEW- "Quantitative mass spectrometry-based assay development and validation: From small molecules to proteins", Clinical Biochemistry, 2012, article in press, pp. 1-12.*
Pearce S.G. et al., REVIEW- "Noninvasive biomarkers for the diagnosis of steatohepatitis and advanced fibrosis in NAFLD", Biomarker Research, 2013, vol. 1, No. 7, pp. 1-11.*
Athinarayanan S. et al., Non-alcoholic fatty liver disease: Current perspectives and future direction in disease pathogenesis, treatment and diagnosis, Medicinal Chemistry, 2012, vol. 2, No. 5, pp. 1-3.*
Bhattacharyya, T., et al., "Mass Spectrometric Detection of Lipid Oxidation Products in Murine and Human Nonalcoholic Fatty Liver Disease", "AASLD Abstracts", Apr. 2008, p. A753, Abstract No. 59, from Gastroenterology, vol. 134, No. 4, Supplement 1.
Kalhan, S., et al., "Identification of Non-Alcoholic Steatohepatitis (NASH) Using Plasma Metabolome in Humans", "FASEB Journal", Apr. 2008, Page(s) (Abstract), vol. 22.
Achterberg, V., et al., "Metabolism of ether lysophospholipids in Leishmania donovani promastigotes", "Molecular and Biochemical Parasitology", Dec. 1987, pp. 277-287, vol. 26, No. 3.
Albert, C., et al., "Reactive Chlorinating Species Produced by Myeloperoxidase Target the Vinyl Ether Bond of Plasmalogens", "The Journal of Biological Chemistry", Jun. 29, 2001, pp. 23733-23741, vol. 276, No. 26.
Bittman, R., et al., "Synthesis and antitumor properties of a plasmalogen methyl ether analogue", "Tetrahedron", May 14, 2001, pp. 4277-4282, vol. 57, No. 20.
Do, U., et al., "Synthesis of 1-O-[hexadecyl-1',2'-3H]hexadecyl 2-acetyl-sn-glyceryl 3-phosphorylcholine and I-O-alkyl [32p]lysophosphatidycholine", "Journal of Labelled Compounds and Radiopharmaceuticals", Feb. 1996, pp. 117-127, vol. 38, No. 2.

* cited by examiner

*Primary Examiner* — Satyendra Singh
(74) *Attorney, Agent, or Firm* — Hultquist, PLLC; Steven J. Hultquist; Mary B. Grant (57) ABSTRACT

The invention relates to methods for the diagnosis of non-alcoholic steatosis (NASH). The method relies on the determination of certain metabolic markers in a biological sample of the patient which are up- or down-regulated in the NASH patients vs. patients with a simple fatty liver (steatosis).

4 Claims, 3 Drawing Sheets

METHOD FOR THE DIFFERENTIAL DIAGNOSIS OF NON-ALCOHOLIC FATTY LIVER DISEASE BASED ON A METABOLOMIC PROFILE

CROSS-REFERENCE TO RELATED APPLICATIONS

This application is a U.S. national phase under the provisions of 35 U.S.C. §371 of International Patent Application No. PCT/EP2010/063792 filed Sep. 20, 2010, which in turn claims the priority of European Patent Application No. 09382174.2 filed Sep. 22, 2009. The disclosures of such international patent application and European priority patent application are hereby incorporated herein by reference in their respective entireties, for all purposes.

FIELD OF THE INVENTION

The invention relates to the field of diagnostic methods and, more in particular, to a method for the diagnosis of non-alcoholic steatohepatitis (NASH) based on the determination of the levels of a series of metabolic markers which are altered in NASH patients with respect to patients with simple fatty liver (steatosis).

BACKGROUND OF THE INVENTION

Non-alcoholic fatty liver disease (NAFLD) encompasses a wide range of conditions characterised by the build-up of fat in the liver cells of people who do not drink alcohol excessively. At one end of the scale is the relatively harmless simple fatty liver, or steatosis, that does not cause significant liver damage. If left unattended this condition may progress to more advanced conditions, some of which may be life threatening. Non-alcoholic steatohepatitis (NASH) is a significant development in NAFLD, corresponding to an aggressive condition characterised by swelling and tenderness in the liver. With intense, on-going inflammation a build up of scar tissue (fibrosis) may form, eventually leading to cirrhosis where irregular bumps, known as nodules, replace the smooth liver tissue and the liver becomes harder. The effect of this, together with continued scarring from fibrosis, means that the liver will run out of healthy cells to support normal functions. This can lead to complete liver failure. Most people with a fatty liver are overweight or obese. As more and more people lead inactive lives and carry extra weight around with them, so the number of cases of fatty liver, in particular NASH, is rising. Therefore, there is a need for diagnostic tests that may provide a robust assessment of the presence of NASH or steatosis in a patient.

There is currently no specific laboratory test for NASH, making it extremely difficult to diagnose since even people who go on to develop fibrosis and cirrhosis may undergo liver damage for many years before symptoms become apparent.

NAFLD may be suspected in subjects with one or more components of the metabolic syndrome, especially obesity and type 2 diabetes, and elevated serum aminotransferase levels [alanine aminotransferase (ALT) and aspartate aminotransferase (AST)] in the absence of alcohol abuse or other common causes of liver disease. The only widely accepted test for distinguishing NASH from other forms of disease is a liver biopsy. This process involves passing a fine hollow needle through the skin and into the liver, withdrawing a small tissue of sample that is submitted for histological examination. Apart from the obvious discomfort induced by this invasive procedure, assessment is often subjective and prone to sampling error.

Several methods for the detection of NAFLD have been described to date based on measuring physico-chemical properties. For instance, scanning the liver with imaging equipment (MRI) allows the detection of fat deposits (steatosis) in the liver. WO08041128 describes a method for the diagnosis of NASH based on the determination of the electrical impedance of the liver using a pair of electrodes that are placed in contact with the liver using an open abdominal surgical procedure (laparotomy). However, this method requires direct contact of the electrodes with the liver, making it more appropriate for the detection of NASH in explanted livers before they are transplanted into a receptor, and does not allow the distinction between the different stages of NAFLD.

Transient elastography or FibroScan (Castera L, et al., 2006, *Hepatology* 43:373-374) has been proposed for the non-invasive diagnosis of liver fibrosis. Its main application is to avoid liver biopsy in assessing disease progression in patients with chronic hepatitis C.

Several predictive panels based on the multivariate analysis of well-established clinical and laboratory variables (such as age, body mass index (BMI), ALT, AST, glucose, insulin resistance, albumin) have been proposed as non-invasive markers for the quantitative assessment of fibrosis (FibroTest, NAFLD fibrosis score), steatosis (SteatoTest) and NASH (NashTest) and more recently the ELF test for the assessment of liver fibrosis in patients with NAFLD (Guha I N, et al., 2008, *Hepatology* 47:455-460).

Other methods are based on the presence of different polymorphisms in genes involved in lipid metabolism. These polymorphisms may be detected in body fluids and, thus, they can be considered as non- or minimally-invasive methods. For instance, WO06117945 describes a method for the diagnosis of NASH by detecting the T94A genetic polymorphism in FABP1 in a biological sample taken from a subject.

Other methods are based on the determination of the expression levels of one or more proteins or metabolites in body fluids. In particular, WO06082522 describes a method for detecting steatosis in a patient by determining the levels of ApoA1, α2-macroglobulin, alanine aminotransferase, gammaglutamyl transpeptidase and triglycerides.

WO08021192 describes a non-invasive method for the diagnosis and monitoring of liver diseases such as NASH and steatosis based on the determinination of levels of fatty acids and eicosanoids in a body fluid of the patient. However, this method is limited to the identification of lipid species and requires complex fractionation steps of the body fluids before the metabolites can be detected.

Lelliot et al (FASEB J., 2005, 19: 1108-1119) describe a method for detecting tamoxifen-induced NASH based on the determination of metabolic profiles in blood using [$^1$H]-NMR. However, this method is performed in samples obtained by liver biopsy and thus, it is a highly invasive method.

WO07136822 describes a method for the detection of NASH from other NAFLD by determining the phosphorylation state of one or more members of the AKT/mTOR/IRS pathway in adipose tissue from a subject. However, this method requires the extraction of an adipose tissue sample from a patient, thus resulting in a minimally invasive method.

Cleary there is a need for non-invasive methods as alternatives to existing diagnosis methods, reducing patient discomfort and hospital-stay costs whilst providing a more robust, standardised assessment.

SUMMARY OF THE INVENTION

In a first aspect, the invention relates to a method for the differential diagnosis of the type of NAFLD in a patient comprising determining in a biological sample of said patient the level(s) of one or more of the metabolic markers defined in table 2 and comparing the levels of said markers with the levels of the same markers in a NASH-positive sample and/or in a steatosis-positive sample wherein
  (i) the patient is diagnosed as having NASH when the levels of one or more of the metabolic marker or markers at positions 1 to 3 and/or 5 to 11 in table 2 are increased with respect to the level of the same metabolic markers in a steatosis-positive sample and/or when the levels of the metabolic marker at position 4 defined in table 2 is decreased with respect to the level of the same metabolic markers in a steatosis-positive sample and/or
  (ii) the patient is diagnosed as having steatosis when the levels of one or more of the metabolic marker or markers in positions 1 to 3 and/or 5 to 11 defined in table 2 are decreased with respect to the level of the same metabolic markers in a NASH-positive sample and/or when the levels of the metabolic marker in position 4 in table 2 is increased with respect to the level of the same metabolic markers in a NASH-positive sample.

In a second aspect, the invention relates to a method for the determination of the efficacy of a therapy for NASH comprising determining in a biological sample of a subject suffering from NASH and having been treated with said therapy the level(s) of one or more of the metabolic markers as defined in table 2 wherein the therapy is considered as effective for the treatment of NASH when the levels of one or more of the metabolic marker(s) defined in positions 1 to 3 and/or 5-11 in table 2 is/are decreased with respect to the level of the same metabolic marker(s) in a reference sample and/or when the levels of the metabolic marker at position 4 in table 2 is increased with respect to the level of the same metabolic marker(s) in a reference sample.

In a third aspect, the invention relates to a method for the identification of compounds suitable for the treatment of NASH comprising determining in a biological sample of a subject suffering from NASH and having been treated with a candidate compound the level(s) of one or more of the metabolic markers as defined in table 2 wherein the compound is considered as effective for the treatment of NASH or steatosis when the levels of one or more of the metabolic marker(s) defined in positions 1 to 3 and/or 5-11 in table 2 is/are decreased with respect to the level of the same metabolic marker(s) in a reference sample and/or when the levels of the metabolic marker at position 4 in table 2 is increased with respect to the level of the same metabolic marker(s) in a reference sample.

In a fourth aspect, the invention relates to a method for the identification of compounds capable of inducing NASH comprising determining in a biological sample of subject which has been treated with a candidate compound the level(s) of one or more of the metabolic markers as defined in table 2 wherein the compound is considered as capable of inducing NASH when the levels of one or more of the metabolic marker(s) defined in positions 1 to 3 and/or 5-11 in table 2 is/are increased with respect to the level of the same metabolic marker(s) in a reference sample and/or when the levels of the metabolic marker at position 4 in table 2 is decreased with respect to the level of the same metabolic marker(s) in a reference sample.

DETAILED DESCRIPTION OF THE INVENTION

I. Diagnosis of NASH

The authors of the present invention have taken a significant step to addressing the need for non-invasive methods for the diagnosis of NASH by performing metabolic profiling of patient serum samples as a non-invasive alternative for NASH diagnosis. The authors of the present invention have identified a series of metabolic markers present in the serum of patients suffering from NASH which are present at different levels with respect to the serum of patients with simple fatty liver (steatosis). These metabolic markers can then be used in a rapid non-invasive diagnostic method for NASH.

Thus, in a first aspect, the invention relates to a method (hereinafter first method of the invention) for the differential diagnosis of the type of NAFLD in a patient comprising determining in a biological sample of said patient the level(s) of one or more of the metabolic markers defined in table 2 and comparing the levels of said markers with the levels of the same markers in a NASH-positive sample and/or in a steatosis-positive sample wherein
  (i) the patient is diagnosed as having NASH when the levels of one or more of the metabolic marker or markers at positions 1 to 3 and/or 5 to 11 in table 2 are increased with respect to the level of the same metabolic markers in a steatosis-positive sample and/or when the levels of the metabolic marker at position 4 defined in table 2 is decreased with respect to the level of the same metabolic markers in a steatosis-positive sample and/or
  (ii) the patient is diagnosed as having steatosis when the levels of one or more of the metabolic marker or markers in positions 1 to 3 and/or 5 to 11 defined in table 2 are decreased with respect to the level of the same metabolic markers in a NASH-positive sample and/or when the levels of the metabolic marker in position 4 in table 2 is increased with respect to the level of the same metabolic markers in a NASH-positive sample.

The expression "method for differential diagnosing" as referred to in accordance with the present invention means that the method may essentially consist of the aforementioned steps or may include further steps. However, it is to be understood that the method, in a preferred embodiment, is a method carried out in vitro, i.e. not practiced on the human or animal body. Diagnosing as used herein refers to assessing the probability according to which a subject is suffering from a disease. As will be understood by those skilled in the art, such an assessment, although preferred to be, may usually not be correct for 100% of the subjects to be diagnosed. The term, however, requires that a statistically significant portion of subjects can be identified as suffering from the disease or as having a predisposition therefore. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 50%, at least 60%, at least 70%, at least 80%, at least 90% at least 95%. The p-values are, preferably, 0.2, 0.1, 0.05.

The term "NAFLD", as used herein, relates a group of conditions having in common the accumulation of fat in the hepatocytes. NAFLD ranges from simple fatty liver (steatosis), to nonalcoholic steatohepatitis (NASH), to cirrhosis (irreversible, advanced scarring of the liver). The term "NASH", as used herein, collectively refers to the state where the liver develops a hepatic disorder (e.g., inflammation, ballooning, fibrosis, cirrhosis, or cancer), or the state where the liver may induce such a pathological condition, and "NASH" is distinguished from "simple steatosis"; i.e., a condition in which fat is simply accumulated in the liver, and which does not progress to another hepatic-disorder-developing condition.

The term "metabolic marker", as used herein, refers to small molecule compounds, such as substrates for enzymes of metabolic pathways, intermediates of such pathways or the products obtained by a metabolic pathway. Metabolic pathways are well known in the art and may vary between species. Preferably, said pathways include at least citric acid cycle, respiratory chain, photosynthesis, photorespiration, glycolysis, gluconeogenesis, hexose monophosphate pathway, oxidative pentose phosphate pathway, production and β-oxidation of fatty acids, urea cycle, amino acid biosynthesis pathways, protein degradation pathways such as proteasomal degradation, amino acid degrading pathways, biosynthesis or degradation of: lipids, polyketides (including e.g. flavonoids and isoflavonoids), isoprenoids (including e.g. terpenes, sterols, steroids, carotenoids, xanthophylls), carbohydrates, phenylpropanoids and derivatives, alcaloids, benzenoids, indoles, indole-sulfur compounds, porphyrines, anthocyans, hormones, vitamins, cofactors such as prosthetic groups or electron carriers, lignin, glucosinolates, purines, pyrimidines, nucleosides, nucleotides and related molecules such as tRNAs, microRNAs (miRNA) or mRNAs. Accordingly, small molecule compound metabolites are preferably composed of the following classes of compounds: alcohols, alkanes, alkenes, alkines, aromatic compounds, ketones, aldehydes, carboxylic acids, esters, amines, imines, amides, cyanides, amino acids, peptides, thiols, thioesters, phosphate esters, sulfate esters, thioethers, sulfoxides, ethers, or combinations or derivatives of the aforementioned compounds. The small molecules among the metabolites may be primary metabolites which are required for normal cellular function, organ function or animal growth, development or health. Moreover, small molecule metabolites further comprise secondary metabolites having essential ecological function, e.g. metabolites which allow an organism to adapt to its environment. Furthermore, metabolites are not limited to said primary and secondary metabolites and further encompass artificial small molecule compounds. Said artificial small molecule compounds are derived from exogenously provided small molecules which are administered or taken up by an organism but are not primary or secondary metabolites as defined above. For instance, artificial small molecule compounds may be metabolic products obtained from drugs by metabolic pathways of the animal. Moreover, metabolites further include peptides, oligopeptides, polypeptides, oligonucleotides and polynucleotides, such as RNA or DNA. More preferably, a metabolite has a molecular weight of 50 Da (Dalton) to 30,000 Da, most preferably less than 30,000 Da, less than 20,000 Da, less than 15,000 Da, less than 10,000 Da, less than 8,000 Da, less than 7,000 Da, less than 6,000 Da, less than 5,000, Da, less than 4,000 Da, less than 3,000 Da, less than 2,000 Da, less than 1,000 Da, less than 500 Da, less than 300 Da, less than 200 Da, less than 100 Da. Preferably, a metabolite has, however, a molecular weight of at least 50 Da. Most preferably, a metabolite in accordance with the present invention has a molecular weight of 50 Da up to 1,500 Da. In preferred embodiments, the metabolic markers that can be used in the context of the present invention are those markers indicated in table 2.

The markers suitable for use in the method of the present invention are those defined at positions 1 to 11 in table 2 and corresponding to:

Metabolite 1:

The metabolite corresponding to the plasmalogen known as PC(P-18:0/0:0) or 1-(1Z-octadecenyl)-sn-glycero-3-phosphocholine, having the structure:

and a molecular weight of 507.7 Da

Metabolite 2:

The metabolite corresponds to the plasmalogen known as PC(P-16:0/0:0) or 1-(1Z-hexadecenyl)-sn-glycero-3-phosphocholine, having the structure:

10 and a molecular weight of 479.6 Da.

Metabolite 3:

The metabolite corresponds to the plasmalogen known as PC(P-16:0/20:4) or 1-(1Z-hexadecenyl)-2-(5Z,8Z,11Z,14Z-eicosatetraenoyl)-sn-glycero-3-phosphocholine, having the structure and a molecular weight of 766.1 Da Metabolite 4:

The metabolite corresponds to a sphingomyelin known as SM(d18:2/15:0) or N-(pentadecanoyl)-sphinga-4,6-dienine-1-phosphocholine, having the structure:

and a molecular weight of 673.0 Da.

Metabolite 5

The metabolite corresponds to sulfoglycolithocholate or 2-[[(4R)-4-[(3R,5R,8R,9S,10S,13R,14S,17R)-10,13-dimethyl-3-sulfooxy-2,3,4,5,6,7,8,9,11,12,14,15,16,17-tetradecahydro-1H-cyclopenta[a]phenanthren-17-yl]pentanoyl]amino]acetic acid, having the structure:

and a molecular weight of 513.7 Da.

Metabolite 6

The metabolite corresponds to Hyodeoxycholate-6-O-glucuronide also known as (2S,3S,4S,5R,6R)-3,4,5-trihydroxy-6-[[(3R,5R,6S,8S,9S,10R,13R,14S,17R)-3-hydroxy-17-[(1R)-4-hydroxy-1-methyl-4-oxo-butyl]-10,13-dimethyl-2,3,4,5,6,7,8,9,11,12,14,15,16,17-tetradecahydro-1H-cyclopenta[a]phenanthren-6-yl]oxy]tetrahydropyran-2-carboxylic acid, having the structure and a molecular weight of 568.7 Da Metabolite 7

The metabolite corresponds to trihydroxycoprostanoic acid, also known as (3a,5b,7a,12a)-3,7,12-trihydroxy-Cholestane-5-carboxylic acid and having the structure and a molecular weight of 464.7 Da Metabolite 8

Metabolite 8 corresponds to a molecule having a m/z of 483.3670 and which, under the chromatographic conditions used in the invention, elutes at 5.2 min.

Metabolite 9

Metabolite 9 corresponds to a molecule which [M−H]-ion has a m/z of 467.3728 and which, under the chromatographic conditions used in the invention, elutes at 6 min.

Metabolite 10

Metabolite 10 corresponds to a molecule which [M−H]-ion has a m/z of 467.3719 and which, under the chromatographic conditions used in the invention, elutes at 6.1 min.

Metabolite 11

Metabolite 11 corresponds to a molecule which [M−H]-ion has a m/z of 467.3720 and which, under the chromatographic conditions used in the invention, elutes at 6.2 min.

It will be understood that the first method of the invention can be carried out by determining the level of a variable number of the metabolites defined in table 2 in the biological sample of the subject under study. For example, the level(s) of one biomarker, two or more biomarkers, three or more biomarkers, four or more biomarkers, five or more biomarkers, six or more biomarkers, seven or more biomarkers, eight or more biomarkers, nine or more biomarkers, ten or more biomarkers or eleven biomarkers. The determination of levels of combinations of the biomarkers may allow greater sensitivity and specificity in diagnosing NASH or a predisposition to suffer NASH, and may allow better differentiation of NASH from other diseases that may have similar or overlapping biomarkers.

In a preferred embodiment, the first method of the invention involves the determination of the eleven metabolites mentioned in Table 2. In a preferred embodiment, the first method of the invention involves the determination of the markers found at positions 1 to 7 as defined in table 2, i.e. PC(O-18:1/0:0), PC(O-16:1/0:0), PC(O-16:1/20:4), SM(d1 8:2/15:0), sulfoglycolithocholate, hyodeoxycholate-6-O-glucuronide and trihydroxycoprostanoic acid.

"Sample" or "biological sample" means biological material isolated from a subject. The biological sample may contain any biological material suitable for detecting the desired biomarker and may comprise cellular and/or non-cellular material from the subject. The sample can be isolated from any suitable biological tissue or fluid such as, for example, prostate tissue, blood, blood plasma, serum, urine or cerebral spinal fluid (CSF). Preferably, the samples used for the determination of the metabolite profiles are samples which can be obtained using minimally invasive procedures. In a preferred embodiment, the samples are serum samples.

It will be understood that the biological sample can be analyzed as such or, alternatively, the metabolites may be first extracted from the sample prior to analysis and then the metabolite extract is then analyzed. If the metabolites are extracted prior to analysis, different extraction methods are available to the skilled person. The selection of one or other extraction method will depend on the class of metabolites/small molecules that are targeted from a particular analysis. Suitable extraction methods include "Extraction of free metabolite pools", "Vapor Phase Extraction", and "Total Metabolite Extraction". The first type of extraction, "Extraction of free metabolite pools", is mainly used in metabolomics research. In this case free intracellular metabolite pools are obtained from a biological sample through methanol-water extraction for polar metabolites, or chloroform extraction for non-polar metabolites. The second type of extraction, "Vapor Phase Extraction", refers to the extraction of metabolites that are volatile at room temperature. The metabolites are expelled from the biological sample in the vapor phase. These metabolites are either measured directly by connecting the flask or reactor in which the vapors are generated to the analytical instrument or by absorbing first the vapors in charcoal/solvent and then analyzing the acquired solution. The third type of extraction, "Total Metabolite Extraction", refers to the extraction of the free metabolite pools along with the metabolites that have been incorporated in cellular macromolecules, e.g. lipids, proteins etc. The present invention provides extraction of a particular class of metabolites from macromolecules (e.g. amino acids from proteins or sugars from cell wall components). The present invention also provides a combined high-throughput method which extracts all metabolites simultaneously.

Alternatively, the metabolite quantification can be carried out directly in the biological sample. In this case, the sample may be prepared to enhance detectability of the markers. For example, to increase the detectability of markers, a blood serum sample from the subject can be preferably fractionated by, e.g., Cibacron blue agarose chromatography and single stranded DNA affinity chromatography, anion exchange chromatography, affinity chromatography (e.g., with antibodies) and the like. The method of fractionation depends on the type of detection method used. Any method that enriches for the metabolite of interest can be used. Typically, preparation involves fractionation of the sample and collection of fractions determined to contain the biomarkers. Methods of pre-fractionation include, for example, size exclusion chromatography, ion exchange chromatography, heparin chromatography, affinity chromatography, sequential extraction, gel electrophoresis and liquid chromatography.

The analytes also may be modified prior to detection. These methods are useful to simplify the sample for further analysis. For example, it can be useful to remove high abundance proteins, such as albumin, from blood before analysis.

In yet another embodiment, a sample can be pre-fractionated by removing proteins that are present in a high quantity or that may interfere with the detection of markers in a sample. Proteins in general may be removed by using conventional techniques such as precipitation using organic solvents such as methanol precipitation, ethanol, acetonitrile, acetone or combinations thereof, in particular, combination of methanol, acetone and acetonitrile, acid precipitation using, for example, trichloroacetic acid or perchloric acid, heat denaturation and any combination of organic solvent, acid and heat precipitation. In the case of a blood or serum sample, serum albumin or other proteins abundant in serum such as apolipoproteins, glycoproteins, immunoglobulins may obscure the analysis of markers since they are present in a high quantity. Thus, it may be sufficient to remove one or more of the above proteins albumin in order to detect the metabolites or minor proteins. For this purpose, the blood serum sample can be pre-fractionated by removing serum albumin. Serum albumin can be removed using a substrate that comprises adsorbents that specifically bind serum albumin. For example, a column which comprises, e.g., Cibacron blue agarose (which has a high affinity for serum albumin) or anti-serum albumin antibodies can be used. In yet another embodiment, a sample can be pre-fractionated by isolating proteins that have a specific characteristic, e.g. are glycosylated. For example, a blood serum sample can be fractionated by passing the sample over a lectin chromatography column (which has a high affinity for sugars). Many types of affinity adsorbents exist which are suitable for pre-fractionating blood serum samples. An example of one other type of affinity chromatography available to pre-fractionate a sample is a single stranded DNA spin column. These columns bind proteins which are basic or positively charged. Bound proteins are then eluted from the column using eluants containing denaturants or high pH. Thus there are many ways to reduce the complexity of a sample based on the binding properties of the proteins in the sample, or the characteristics of the proteins in the sample.

In yet another embodiment, a sample can be fractionated using a sequential extraction protocol. In sequential extraction, a sample is exposed to a series of adsorbents to extract different types of biomolecules from a sample.

The method of the invention includes the step of determining the levels of the metabolic marker or marker(s) in a sample and comparing said levels to the levels of the same markers in a reference sample wherein said reference sample is either a steatosis-positive sample or a NASH-positive sample. The terms "steatosis-positive sample" or "NASH-positive sample" relate, respectively, to samples isolated from patients which have been diagnosed with any of these conditions. Preferably, the diagnosis has been carried out by liver biopsy so that the patient is classified as suffering fatty liver or steatosis if the tissue shows fat without inflammation and damage whereas the patient is classified as having NASH when microscopic examination of the tissue shows fat along with inflammation and damage to liver cells. The steatosis-positive sample and/or the NASH-positive sample may result from the pooling of samples from one individual or a population of two or more individuals. The population, for example, may comprise three, four, five, ten, 15, 20, 30, 40, 50 or more individuals.

The levels of the metabolite or metabolites under study in the "reference sample" may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). Such reference levels may also be tailored to specific techniques that are used to measure levels of biomarkers in biological samples (e.g., LC-MS, GC-MS, etc.), where the levels of biomarkers may differ based on the specific technique that is used. In a preferred embodiment, the reference sample is obtained from a healthy subject or from a subject without previous history of NAFLD.

A metabolic marker is considered to be increased in a sample from the subject under study when the levels are increased with respect to the reference sample by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%: by at least 85%, by at least 90%, by at least 95%, by at least 100%, by at least 110%, by at least 120%, by at least 130%, by at least 140% by at least 150%, or more. Similarly, the metabolic marker is considered to be decreased when its levels are decreased with respect to a reference sample by at least 5%, by at least 10%, by at least 15%, by at least 20%, by at least 25%, by at least 30%, by at least 35%, by at least 40%, by at least 45%. by at least 5094, by at least 55%. by at least 60%, by at least 65%, by at least 70%. by at least 75%, by at least 80%, by at least 85%, by at least 90%, by at least 95%, or by 100% (i.e., absent).

Moreover, the determination of the metabolites in the methods according to the present invention, comprises, preferably, a step of separation of the metabolites present in the sample prior to the analysis step. Preferably, said compound separation step yields a time resolved separation of the metabolites comprised by the sample. Suitable techniques for separation to be used preferably in accordance with the present invention, therefore, include all chromatographic separation techniques The term "chromatography", as used herein, refers to a method for mixture component separation that relies on differences in the flowing behavior of the various components of a mixture/solution carried by a mobile phase through a support/column coated with a certain stationary phase. Specifically, some components bind strongly to the stationary phase and spend longer time in the support, while other components stay predominantly in the mobile phase and pass faster through the support. The criterion based on which the various compounds are separated through the column is defined by the particular problem being investigated and imposed by the structure, composition and binding capacity of the stationary phase. For example, a stationary phase could be constructed such that the linear and low molecular weight molecules elute faster than the aromatic and high-molecular weight ones. As the components elute from the support, they can be immediately analyzed by a detector or collected for further analysis. A vast number of separation methods, and in particular chromatography methods, are currently available, including Gas Chromatography ("GC"), Liquid Chromatography ("LC"), Ion Chromatography ("IC"), Size-Exclusion Chromatography ("SEC"), Supercritical-Fluid Chromatography ("SFC"), Thin-Layer Chromatography ("TLC"), High Performance Liquid Chromatography ("HPLC") and Capillary Electrophoresis ("CE"). Gas Chromatography, can be used to separate volatile compounds. Liquid chromatography ("LC") is an alternative chromatographic technique useful for separating ions or molecules that are dissolved in a solvent. The principle of GC and LC separation is the same, their main difference lies on the phase in which the separation occurs (vapor vs. liquid phase). In addition, GC is used primarily to separate molecules up to 650 atomic units heavy, while, in principle, a LC can separate any molecular weight compounds. Suitable types of liquid chromatography that can be applied in the method of the invention include, without limitation, reverse phase chromatography, normal phase chromatography, affinity chromatography, ion exchange chromatography, hydrophilic interaction liquid chromatography (HILIC), size exclusion chromatography and chiral chromatography. These techniques are well known in the art and can be applied by the person skilled in the art without further ado.

In a still more preferred embodiment, the biological sample is fractionated by liquid chromatography prior to the determination of the levels of the metabolic marker or markers. In a preferred embodiment, the liquid chromatography is performed on a C8 column at 40° C. The column may be eluted with a 10 minute linear gradient using a mobile phase at a flow rate of 140 µL/min, consisting of 100% solvent A (typically 0.05% formic acid) for 1 minute followed by an incremental increase of solvent B (typically acetonitrile containing 0.05% formic acid) up to 50% over a further minute, increasing to 100% B over the next 6 minutes before returning to the initial composition in readiness for the subsequent injection which proceeded a 45 s system re-cycle time. The volume of sample injected onto the column may be of 1 µL.

Once the sample has been processed, the first method of the invention involves the determination of the levels of the metabolite in the sample. The expression "determining the levels of a metabolite", as used herein, refers to ascertaining the absolute or relative amount or concentration of the metabolite in the sample. There are many ways to collect quantitative or relational data on metabolites, and the analytical methodology does not affect the utility of metabolite concentrations in predicting phenotype or assessing metabolism. Suitable methods for determining the levels of a given metabolite include, without limitation, refractive index spectroscopy (R1), Ultra-Violet spectroscopy (UV), fluorescent analysis, radiochemical analysis, Near-InfraRed spectroscopy (ear-IR), Nuclear Magnetic Resonance spectroscopy (NMR), Light Scattering analysis (LS), Mass Spectrometry, Pyrolysis Mass Spectrometry, Nephelometry, Dispersive Raman Spectroscopy, gas chromatography combined with mass spectroscopy, liquid chromatography combined with mass spectroscopy, MALDI combined with mass spectroscopy, ion spray spectroscopy combined with mass spectroscopy, capillary electrophoresis, NMR and IR detection.

In a preferred embodiment, the determination of the metabolite levels is carried out by mass spectrometry. As used herein, "mass spectrometry" (MS analysis) refers to an analytical technique to identify unknown compounds including: (1) ionizing the compounds and potentially fractionating the compounds parent ion formed into daughter ions; and (2) detecting the charged compounds and calculating a mass-to-charge ratio (m/z). The compounds may be ionized and detected by any suitable means. A "mass spectrometer" includes means for ionizing compounds and for detecting charged compounds.

Preferably, mass spectrometry is used in particular gas chromatography mass spectrometry (GC-MS), liquid chromatography mass spectrometry (LC-MS), direct infusion mass spectrometry or Fourier transform ion-cyclotron-resonance mass spectrometry (FT-ICR-MS), capillary electrophoresis mass spectrometry (CE-MS), high-performance liquid chromatography coupled mass spectrometry (HPLC-MS), quadrupole mass spectrometry, any sequentially coupled mass spectrometry, such as MS-MS or MS-MS-MS, inductively coupled plasma mass spectrometry (ICP-MS), pyrolysis mass spectrometry (Py-MS), ion mobility mass spectrometry or time of flight mass spectrometry (TOF), of electrospray ionization mass spectrometry (ESI-MS), ESI-MSMS, ESI-MS/(MS)$^n$, matrix-assisted laser desorption ionization time-of-flight mass spectrometry (MALDI-TOF-MS), surface-enhanced laser desorption/ionization time-of-flight mass spectrometry (SELDI-TOFMS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MSIMS, APCI-(MS)$^n$, atmospheric pressure photoionization mass spectrometry (APPI-MS), APPI-MSIMS, and APPI-(MS)$^n$, quadrupole mass spectrometry, fourier transform mass spectrometry (FTMS), and ion trap mass spectrometry, where n is an integer greater than zero. Most preferably, LC-MS is used as described in detail below. Said techniques are disclosed in, e.g., Nissen, Journal of Chromatography A, 703, 1995: 37-57, U.S. Pat. No. 4,540,884 or U.S. Pat. No. 5,397,894, the disclosure content of which is hereby incorporated by reference.

The above mentioned ionization methods generally produce an ion resulting from the addition of one or more atoms or by cleavage of the molecule. These ions can then be used as surrogate markers for the metabolites used in the method of the invention. The term "surrogate marker" as used herein means a biological or clinical parameter that is measured in place of the biologically definitive or clinically most meaningful parameter.

Typically, the ions result from the addition of a proton or a hydrogen nucleus, $[M+H]^+$ where M signifies the molecule of interest, and H signifies the hydrogen ion, which is the same as a proton. Some ionization methods will also produce analogous ions. Analogous ions may arise by the addition of an alkaline metal cation, rather than the proton discussed above. A typical species might be $[M+Na]^+$ or $[M+K]^+$. The analysis of the ionized molecules is similar irrespective of whether one is concerned with a protonated ion as discussed above or dealing with an added alkaline metal cation. The major difference is that the addition of a proton adds one mass unit (typically called one Dalton), in case of the hydrogen ion (i.e., proton), 23 Daltons in case of sodium, or 39 Daltons in case of potassium. These additional weights or masses are simply added to the molecular weight of the molecule of interest and the MS peak occurs at the point for the molecular weight of the molecule of interest plus the weight of the ion that has been added. These ionization methods can also produce negative ions. The most common molecular signal is the deprotonated molecule $[M-H]^-$, in this case the mass is one Dalton lower than the molecular weight of the molecule of interest. In addition, for some compounds it will be produced multiply charged ions. These are of the general identification type of $[M+nH]^{n+}$, where small n identifies the number of additional protons that have been added.

Preferably, the sample (or the eluent when the sample has been fractionated prior to the mass spectrometry) may be introduced into the mass spectrometer (for example, a LCT Premier™, Waters Corp., Milford, USA) by electrospray ionisation, with capillary and cone voltages set in the positive and negative ion modes to 3200 V and 30 V, and 2800 V and 50 V respectively. The nebulization gas may be set to 500 L/h at a temperature of 200° C. The cone gas may be set to 50 L/h and the source temperature to 120° C. Centroid data may be acquired from m/z 50-1000 using an accumulation time of 0.2 s per spectrum. The spectra may be mass corrected in real time by reference to leucine enkephalin, infused at 50 µL/min through an independent reference electrospray, sampled every 10 s. An appropriate test mixture of standard compounds may be analysed before and after the entire set of randomized, duplicated sample injections in order to examine the retention time stability, mass accuracy and sensitivity of the system throughout the course of the run which lasted a maximum of 3 6 h per batch of samples injected.

In a still more preferred embodiment, the biological sample is fractionated by liquid chromatography prior to the determination of the levels of the metabolic marker or markers using the methods defined above.

II. Method for the Determination of the Efficacy of a Therapy for NAFLD

The invention also provides a method for the determination of the efficacy of the therapy for NASH. Thus, in another aspect, the invention relates to a method (hereinafter "the second method of the invention") for the determination of the efficacy of a therapy for NASH comprising determining in a biological sample of a subject suffering from NASH and having been treated with said therapy the level(s) of one or more of the metabolic markers as defined in table 2 wherein the therapy is considered as effective for the treatment of NASH when the levels of one or more of the metabolic marker(s) defined in positions 1 to 3 and/or 5-11 in table 2 is/are decreased with respect to the level of the same metabolic marker(s) in a reference sample and/or when the levels of the metabolic marker at position 4 in table 2 is increased with respect to the level of the same metabolic marker(s) in a reference sample.

The different aspects of the second method of the invention (the methods used for the determination of the levels of the markers, the nature of the sample which is to be studied, the thresholds for consideration of a marker as having been increased or decreased) are essentially as defined previously in respect of the first method of the invention.

In a preferred embodiment, the second method of the invention involves the determination of the eleven metabolites mentioned in Table 2. In a preferred embodiment, the second method of the invention involves the determination of the markers found at positions 1 to 7 as defined in table 2, i.e. PC(O-18:1/0:0), PC(O-16:1/0:0), PC(O-16:1/20:4), SM(d1 8:2/15:0), Sulfoglycolithocholate, Hyodeoxycholate-6-O-glucuronide and trihydroxycoprostanoic acid.

The term "reference sample", as used in respect of the second method of the invention for the determination of the efficacy of a therapy for NASH, relates to either a sample derived from the patient wherein the efficacy of the therapy is being tested but obtained from the patient prior to the administration of the therapy. In another embodiment, the reference sample is a sample from a patient suffering from NASH which has either been left untreated or which has been treated with a control therapy, preferably, the same excipient, carrier or vehicle which is used in the therapy whose efficacy for the treatment of NASH is to be assessed.

III. Method for the Identification of Compounds Suitable for the Treatment of NASH The authors of the present invention have also developed a method for the identification of a compound suitable for the treatment of NASH. The identification of a series of metabolites whose levels are increased or decreased with respect to steatosis-positive samples allows the screening for compounds in a model of NASH which are capable of restoring the levels of the markers to those found in steatosis-positive samples.

Thus, in another aspect, the invention relates to a method (hereinafter "the third method of the invention") for the identification of compounds suitable for the treatment of NASH comprising determining in a biological sample of a subject suffering from NASH and having been treated with a candidate compound the level(s) of one or more of the metabolic markers as defined in table 2 wherein the compound is considered as effective for the treatment of NASH or steatosis when the levels of one or more of the metabolic marker(s) defined in positions 1 to 3 and/or 5-11 in table 2 is/are decreased with respect to the level of the same metabolic marker(s) in a reference sample and/or when the levels of the metabolic marker at position 4 in table 2 is increased with respect to the level of the same metabolic marker(s) in a reference sample.

The different aspects of the third method of the invention (the methods used for the determination of the levels of the markers, the nature of the sample which is to be studied, the thresholds for consideration of a marker as having been increased or decreased) are essentially as defined previously in respect of the first method of the invention.

In a preferred embodiment, the third method of the invention involves the determination of the eleven metabolites mentioned in Table 2. In a preferred embodiment, the third method of the invention involves the determination of the markers found at positions 1 to 7 as defined in table 2, i.e. PC(O-18:1/0:0), PC(O-16:1/0:0), PC(O-16:1/20:4), SM(d1

8:2/15:0), Sulfoglycolithocho late, Hyodeoxycholate-6-O-glucuronide and trihydroxycoprostanoic acid.

The term "reference sample", as used in respect of the third method of the invention, relates to either a sample derived from the patient wherein the therapy is being tested but obtained from the patient prior to the administration of the therapy. In another embodiment, the reference sample is a sample from a patient suffering from NASH which has either been left untreated or which has been treated with a control therapy, preferably, the same excipient, carrier or vehicle which is used in the candidate compound which is being screened.

The term "therapy" as used herein, encompasses the treatment of existing NASH as well as preventative treatment (i.e., prophylaxis). Therapy includes, but is not limited to, administering an agent for treating NASH, treating associated metabolic conditions such as diabetes and hyperlipidemia, improving insulin resistance, following a balanced and healthy diet, avoiding alcohol, and avoiding unnecessary medications.

Examples of suitable animals for use in the screening method of the invention include, but are not limited to, mice, rats, rabbits, monkeys, guinea pigs, dogs and cats. In accordance with this embodiment, the test compound or a control compound is administered (e.g., orally, rectally or parenterally such as intraperitoneally or intravenously) to a suitable animal and the effect on the levels of one or more of the metabolites shown in tables 2 or 3 is determined. Examples of agents include, but are not limited to, nucleic acids (e.g., DNA and RNA), carbohydrates, lipids, proteins, peptides, peptidomimetics, small molecules and other drugs. Agents can be obtained using any of the numerous approaches in combinatorial library methods known in the art. Test compounds further include, for example, antibodies (e.g., polyclonal, monoclonal, humanized, anti-idiotypic, chimeric, and single chain antibodies as well as Fab, F(ab') 2, Fab expression library fragments, and epitope-binding fragments of antibodies). Further, agents or libraries of compounds may be presented, for example, in solution, on beads, chips, bacteria, spores, plasmids or phage.

If the compound is a low-molecular weight compound, then this can be generated by various methods known to the art, preferably synthetically, in particular by combinatorial chemistry, or by biochemical methods, in particular by recombinant expression or purification from biological probes. The compound is of low molecular weight ("small molecules") or the library is composed of molecules with low molecular weight ("small molecule library"). A "small molecule" is defined as a complex collection of compounds, which are produced in a non-biological way, that means which are not produced by recombinant expression, like for instance most protein or peptide libraries. "Small molecules" can be generated by various methods known to the art, but are preferably produced by synthetically, more preferably by combinatoric chemistry, to generate a compound library with a maximum chemical diversity within the constraints of predicted attractive drug characteristics. If the compound to be assayed for its suitability for the treatment of NASH is a peptide or a peptide library, then these can be generated by various methods known to the art for their use as candidate compounds, but they are preferably produced by biochemical methods, more preferably by recombinant expression in prokaryotic or eukaryotic cells.

The compound to be tested for its suitability for the therapy of NASH can be formulated with a pharmaceutically acceptable carrier to produce a pharmaceutical composition, which can be administered to a human or other animal. A pharmaceutically-acceptable carrier can be, for example, water, sodium phosphate buffer, phosphate-buffered saline, normal saline or Ringer's solution or other physiologically-buffered saline, or other solvent or vehicle such as a glycol, glycerol, an oil such as olive oil or an injectable organic ester. A pharmaceutically acceptable carrier can also contain physiologically acceptable compounds that act, for example, to stabilize or increase the absorption of the modulatory compound. One skilled in the art would know that the choice of a pharmaceutically acceptable carrier, including a physiologically acceptable compound, depends, for example, on the route of administration of the composition.

IV. Method for the Identification of Compounds Capable of Inducing NAFLD in a Subject The identification of a profile of metabolic markers whose levels are altered in patients suffering from NASH with respect to subjects with simple fatty liver (steatosis) can be used in a method for the identification of compounds capable of inducing NASH in a subject by contacting a steatosis-positive subject with a compound suspected of causing NASH and measuring the variation in the levels of one or more of the markers indicated in table 2.

Thus, in another aspect, the invention relates to a method (hereinafter "the fourth method of the invention") for the identification of compounds capable of inducing NASH comprising determining in a biological sample of subject which has been treated with a candidate compound the level(s) of one or more of the metabolic markers as defined in table 2 wherein the compound is considered as capable of inducing NASH when the levels of one or more of the metabolic marker(s) defined in positions 1 to 3 and/or 5-11 in table 2 is/are increased with respect to the level of the same metabolic marker(s) in a reference sample and/or when the levels of the metabolic marker at position 4 in table 2 is decreased with respect to the level of the same metabolic marker(s) in a reference sample.

The different aspects of the fourth method of the invention (the methods used for the determination of the levels of the markers, the nature of the sample which is to be studied, the thresholds for consideration of a marker as having been increased or decreased) are essentially as defined previously in respect of the first method of the invention.

In a preferred embodiment, the fourth method of the invention involves the determination of the eleven metabolites mentioned in Table 2. In a preferred embodiment, the fourth method of the invention involves the determination of the markers found at positions 1 to 7 as defined in table 2, i.e. PC(O-18:1/0:0), PC(O-16:1/0:0), PC(O-16:1/20:4), SM(d1 8:2/15:0), Sulfoglycolithocholate, Hyodeoxycholate-6-O-glucuronide and trihydroxycoprostanoic acid.

The term "reference sample", as used in respect of the fourth method of the invention, relates to either a sample derived from the subject wherein the effect of a candidate compound is tested obtained prior to the administration of the candidate compound. In another embodiment, the reference sample is a sample from a steatosis-positive subject which has either been left untreated or which has been treated with a control therapy, preferably, the same excipient, carrier or vehicle which is used in the candidate compound which is being screened.

The invention is described herein by way of the following examples which are to be construed as merely illustrative and not limitative of the invention.

EXAMPLES

Materials and Methods

Patients.

In an initial pilot study used to explore metabolic differences between obese NAFLD patients and obese subjects with a normal liver histology, 15 serum samples were analyzed: 5 obese females with a normal liver histology (age 35.4+0.4 years; BMI 42.8+0.4 kg/m$^2$; ALT 16.6+1.0 U/L; AST 17.4+0.5 U/L; glucose 5.0+0.1 mM), 5 obese females with a histological diagnosis of steatosis grade S3 (age 33.4+ 2.1 years; BMI 45.0+2.3 kg/m$^2$; ALT 33.2+3.2 U/L; AST 23.4+1.3 U/L; glucose 5.5+0.4 mM), and 5 obese females with a histological diagnosis of NASH grade 1 (age 38.0+4.8 years; BMI 44.3+2.3 kg/m$^2$; AST 54.6+8.9 U/L; ALT 77.4+ 17.1 U/L; glucose 6.4+0.4 mM).

In a separate study a larger set of NAFLD serum samples was examined (Table 1): 54 patients diagnosed with steatosis (33 female, 21 male, age 42.7+1.5 years, BMI 44.6+0.9 kg/m$^2$, ALT 52.3+4.3 U/L, AST 39.7+2.6 U/L, glucose 6.6+ 0.4 mM) and 20 patients diagnosed with early-stage NASH (9 female and 11 male, age 54.5+2.1 years, BMI 29.6+1.3 kg/m$^2$, ALT 78.5+14.9 U/L, AST 63.6+12.1 U/L, glucose 6.1+0.5 mM). The NAFLD diagnosis of a subset (n=10, 6 with steatosis and 4 with NASH, 6 female, 4 male, age 45.0+ 4.9 years, BMI 41.1+2.4 kg/m$^2$, ALT 56.2+13.4 U/L, AST 53.6+11.4 U/L, glucose 5.2+0.5 mM) of these samples was withheld until the data analysis procedure was complete; these samples served as external blind samples useful for testing the predictive value of the NASH biomarkers.

A group of 30 NAFLD plasma samples corresponding to 16 patients with steatosis (13 female and 3 male; age 49.2±1.7 years, BMI 38.4+1.5 kg/m$^2$) and 14 patients with NASH (13 female and 1 male; age 41.0±2.5 years, BMI 37.1+1.6 kg/m$^2$) was also analyzed (Supplementary Table 1). The human research review committee of the four participating hospitals approved the study.

Metabolic Profiling.

A global metabolite profiling UPLC®-MS methodology was employed where all endogenous metabolite related features, characterised by mass-to-charge ratio m/z and retention time Rt, are included in a subsequent multivariate analysis procedure used to study metabolic differences between the different groups of samples[33,34,35,36]. Where possible, Rt-m/z features corresponding to putative biomarkers were later identified.

Sample Preparation.

Serum was prepared by incubating patients' venous blood in serum separator tubes (BD Vacutainer, reference 367957) for 30 minutes before centrifugation (2500 g, 15 min); supernatants were aliquoted into microtubes and stored at −80° C. until required. Plasma was prepared by incubating the blood in coagulation (EDTA) tubes (BD Vacutainer, reference 367863) for 30 minutes before the same centrifugation/supernatant collection/storage protocol as that used for the serum samples was applied.

Proteins were precipitated from the defrosted serum/plasma samples (100 μL) by adding four volumes of methanol in 1.5 mL microtubes at room temperature. After brief vortexing the samples were incubated overnight at −20° C. Supernatants were collected after centrifugation at 13,000 rpm for 10 minutes, dried, and resuspended in 120 μL of 80% methanol. The resulting extracted samples were then transferred to vials for UPLC®-MS analysis.

Chromatography.

Chromatography was performed on a 1 mm i.d.×100 mm ACQUITY™ 1.7 μm C8 BEH column (Waters Corp., Milford, USA) using an ACQUITY™ UPLC® system (Waters Corp., Milford, USA). The column was maintained at 40° C. and eluted with a 10 minute linear gradient. The mobile phase, at a flow rate of 140 μL/min, consisted of 100% solvent A (0.05% formic acid) for 1 minute followed by an incremental increase of solvent B (acetonitrile containing 0.05% formic acid) up to 50% over a further minute, increasing to 100% B over the next 6 minutes before returning to the initial composition in readiness for the subsequent injection which proceeded a 45 s system re-cycle time. The volume of sample injected onto the column was 1 μL.

Mass Spectrometry.

The eluent was introduced into the mass spectrometer (LCT Premier™, Waters Corp., Milford, USA) by electrospray ionisation, with capillary and cone voltages set in the positive and negative ion modes to 3200 V and 30 V, and 2800 V and 50 V respectively. The nebulization gas was set to 500 L/h at a temperature of 200° C. The cone gas was set to 50 L/h and the source temperature set to 120° C. Centroid data were acquired from m/z 50-1000 using an accumulation time of 0.2 s per spectrum. All spectra were mass corrected in real time by reference to leucine enkephalin, infused at 50 μL/min through an independent reference electrospray, sampled every 10 s. An appropriate test mixture of standard compounds was analysed before and after the entire set of randomized, duplicated sample injections in order to examine the retention time stability, mass accuracy and sensitivity of the system throughout the course of the run which lasted a maximum of 3 6 h per batch of samples injected.

Online tandem mass spectrometry (MS/MS) experiments for metabolite identification were performed on a Waters QTOF Premier™ (Waters Corp., Milford, USA) instrument operating in both the positive and negative ion electrospray modes; source parameters were identical to those employed in the profiling experiments, except for the cone voltage which was increased (30-70 V) when pseudo MS/MS/MS data was required. During retention time windows corresponding to the elution of the compounds under investigation the quadrupole was set to resolve and transmit ions with appropriate mass-to-charge values. The selected ions then traversed an argon-pressurized cell, with a collision energy voltage (typically between 5 and 50 V) applied in accordance with the extent of ion fragmentation required. Subsequent TOF analysis of the fragment ions generated accurate mass MS/MS or pseudo MS/MS/MS spectra corrected in real time by reference to leucine enkephalin, infused at 50 μL/min through an independent reference electrospray, sampled every 10 s. Centroid data were acquired between m/z 50-1000 using an accumulation time of 0.08 s per spectrum.

Data Processing.

All data were processed using the MarkerLynx application manager for MassLynx 4.1 software (Waters Corp., Milford, USA). The LC/MS data are peak-detected and noise-reduced in both the LC and MS domains such that only true analytical peaks are further processed by the software (e.g. noise spikes are rejected). A list of intensities (chromatographic peak areas) of the peaks detected is then generated for the first sample, using the retention time (Rt) and m/z data pairs as the identifier for each peak. This process is repeated for each LC-MS run and the data from each LC/MS analysis in the batch are then sorted such that the correct peak intensity data for each Rt-m/z pair are aligned in the final data table. The ion intensities for each peak detected are then normalised, within each sample, to the sum of the peak intensities in that sample. The resulting normalised peak intensities form a single matrix with Rt-m/z pairs for each file in the dataset. All processed data were mean centred and pareto scaled[37] during multivariate data analysis.

Multivariate Data Analysis.

The first objective in the data analysis process is to reduce the dimensionality of the complex data set to enable easy visualisation of any metabolic clustering of the different groups of samples. This has been achieved (FIGS. 1 and 2) by principal components analysis (PCA)[38] where the data matrix is reduced to a series of principal components (PCs), each a linear combination of the original Rt-m/z pair peak areas. Each successive PC explains the maximum amount of variance possible, not accounted for by the previous PCs. Hence the scores plots shown in the figures—where the first two principal components, t[1] and t[2], are plotted—represent the most important metabolic variation in the samples captured by the analysis.

The second stage of the data analysis process concerns the identification of metabolites contributing to the clustering observed in the PCA plots. The orthogonal partial least-squares to latent structures discriminant analysis (OPLS-DA) method was used for this purpose (Wiklund S, et al., 2008, *Anal Chem* 80:115-122 and Bylesjö M, et al., 2006, *J Chemometrics* 20:341-351). This is a supervised approach, focusing the analysis towards the study objective: possible biomarkers discriminating between steatosis and NASH patients. An extra variable Y is created for each sample, taking on discrete values 0 for steatosis grade S1, S2 and S3 samples and 1 for NASH samples. Regression of this data allows new principal components to be calculated, now successively explaining the maximum correlated X-Y variance. Rotation of this PLS model allows inter-class (steatosis—NASH) correlation to be captured in a single predictive component. The performance of this supervised model was evaluated using the $Q^2$ parameter, calculated by iteratively leaving out samples from the model and predicting their Y values. A $Q^2$ score between 0.7-1.0 is indicative of a reliable classifier. Filtration of the loading profile associated with the OPLS-DA predictive component resulted in a set of candidate biomarkers that were further evaluated according to their dependence on a number of different clinical parameters (age, sex, BMI) and concordance between different sets of data (e.g. serum and plasma sample data). It should be noted that the external blind set of samples was not included in the OPLS-DA analysis procedure.

Example 1

Figure 1:
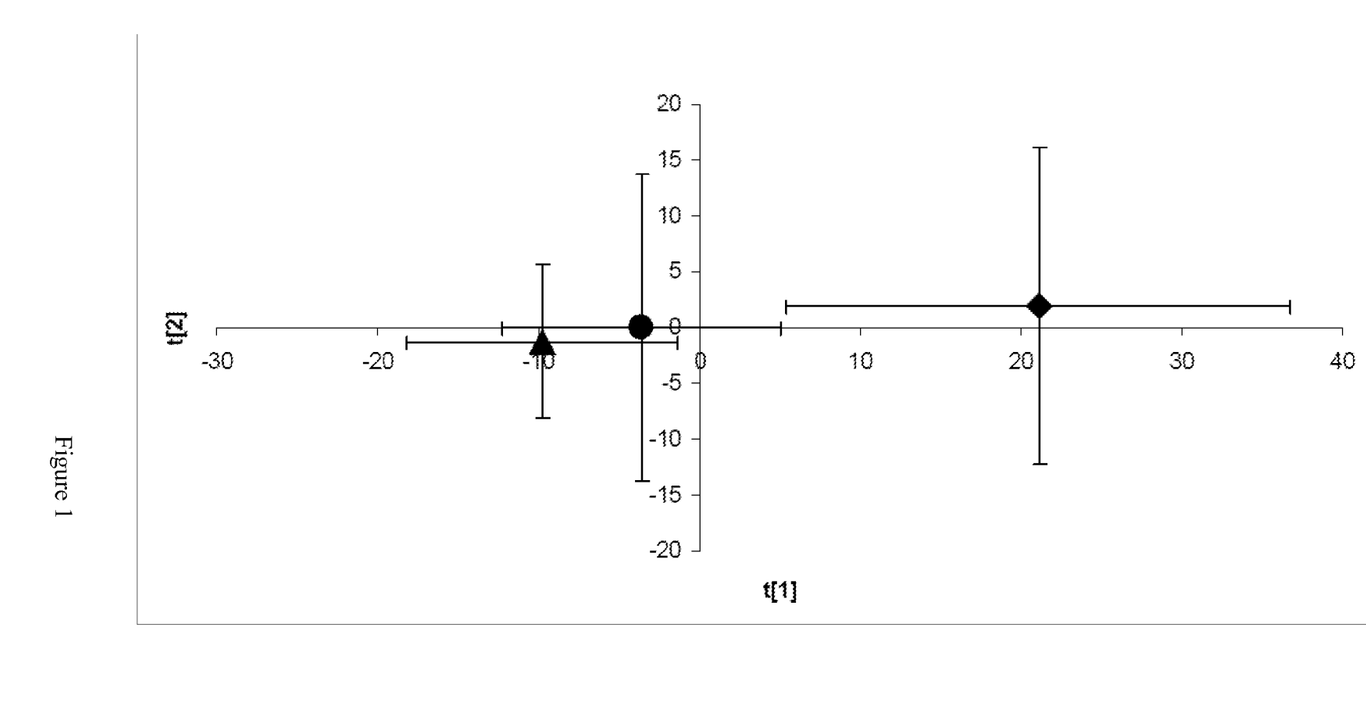
FIG. 1. Mean (±1 standard error of the mean) scores after PCA of the UPLC®-MS serum metabolic profiling data obtained from different groups of obese patients: normal liver (n=5), diamond; steatosis grade 3 (n=5), circle; NASH (n=5), triangle. Significant differences between the normal liver and NAFLD samples are observed—the normal liver samples have a higher, positive score in the first principal component t[1].
Figure 2:
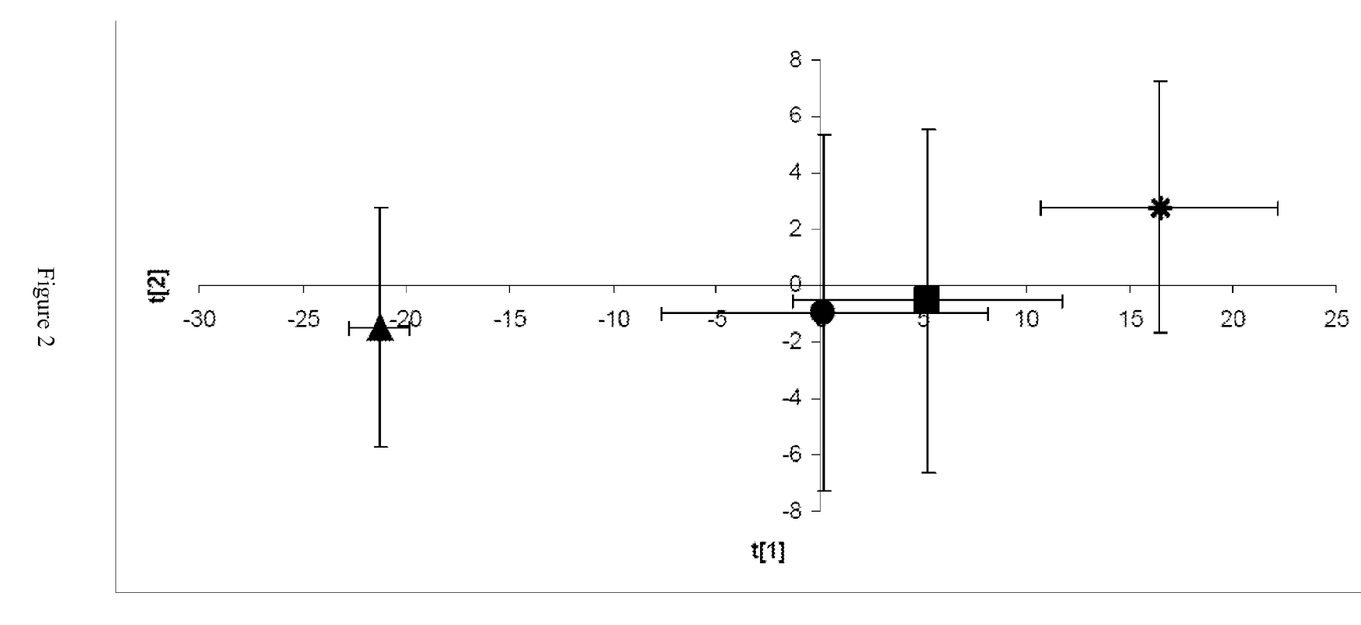
FIG. 2. Mean (±1 standard error of the mean) scores after PCA of the UPLC®-MS serum metabolic profiling data obtained from different groups of NAFLD patients: steatosis grade 1 (n=20), star; steatosis grade 2 (n=18), square; steatosis grade 3 (n=16), circle; NASH (n=20), triangle. Significant differences between the steatosis and NASH samples are observed as well as a clear trajectory of the different grades of steatosis along the first principal component t[1]—less severe NAFLD patients have higher, positive scores.

Metabolic Profiling of Serum Samples Taken from Obese Patients with Normal Liver, Steatosis, or NASH Since it is not known as to what extent obese individuals with normal liver, steatosis or NASH may be considered as discrete metabolic clusters, 15 age, sex and BMI matched serum samples were analyzed by UPLC®-MS (5 with a normal liver histology, 5 with steatosis grade S3, and 5 with NASH grade 1). PCA was used to produce a two-dimensional visual summary of the observed variation in the serum metabolic profiles of these samples (FIG. 1). The results indicate that obese subjects with a normal liver histology and obese NAFLD patients do not cluster together, with normal liver patients having a higher, positive score in the first principal component, t[1]. A less prominent differentiation between the steatosis and NASH patients is also apparent, perhaps suggesting that these conditions may also have distinct metabolic profiles.

Example 2

Extended Metabolic Profiling Study of Serum Samples Collected from Patients with a Histological Diagnosis of Steatosis or NASH.

In order to further investigate the apparent NAFLD metabolic correlation observed in the obese patients, a larger set of serum samples was analyzed. A total of 74 samples were collected from NAFLD patients: 54 with a histological diagnosis of steatosis (20 with steatosis grade S1, 18 with steatosis grade S2, and 16 with steatosis grade S3), and 20 with a histological diagnosis of NASH grade 1 (Table 1). Analysis of the PCA scores plot corresponding to these samples (FIG. 2) reveals a notable separation between the NASH and steatosis patients, where the steatosis patients have a higher, positive score in the first principal component t[1]. This figure also shows a clear trajectory of the different stages of steatosis (S1-S3) along the first principal component—lower grades have a higher, positive score—indicating a metabolic correlation with steatosis progression.

TABLE 1

Clinical details of the NAFLD patients included in the large scale serum sample study

| Group | Female | Male | Age (years) | BMI (kg/m$^2$) | ALT (U/L) | AST (U/L) | Glucose (mM) |
|---|---|---|---|---|---|---|---|
| Steatosis Grade 1 | 12 | 8 | 40.0 + 2.8 | 43.8 + 1.1 | 53.0 + 7.1 | 43.5 + 5.0 | 6.4 + 0.4 |
| Steatosis Grade 2 | 10 | 8 | 45.1 + 1.9 | 45.2 + 2.3 | 45.4 + 6.1 | 35.7 + 4.1 | 7.0 + 1.1 |
| Steatosis Grade 3 | 11 | 5 | 43.4 + 2.8 | 44.9 + 1.5 | 52.3 + 9.1 | 39.8 + 4.5 | 6.5 + 0.7 |
| NASH | 9 | 11 | 54.5 + 2.1 | 29.6 + 1.3 | 78.5 + 14.9 | 63.6 + 12.1 | 6.1 + 0.5 |

Diagnosis of steatosis or NASH was established histologically. Values are given as mean + 1 standard error of the mean.

TABLE 2

Identification of human NASH serum metabolic biomarkers

| Marker | Rt (min) | m/z (Da/e) | Ion | Mass Error (mDa) | Class | Common name | Fold Change | p-value |
|---|---|---|---|---|---|---|---|---|
| 1 | 4.7 | 508.3755 | [M + H]$^+$ | −1.2 | Plasmalogen | PC(P-18:0/0:0) | 1.22 | 0.013 |
| 2 | 4.4 | 524.3342 | [M + CHO$_2$]$^-$ | −1.0 | Plasmalogen | PC(P-16:0/0:0) | 1.15 | 0.026 |
| 3 | 8.0 | 766.5756 | [M + H]$^+$ | +0.5 | Plasmalogen | PC(P-16:0/20:4) | 1.29 | 0.012 |
| 4 | 6.5 | 673.5290 | [M + H]$^+$ | +0.6 | Sphingomyelin | SM(d18:2/15:0) | 0.69 | 0.003 |

TABLE 2-continued

Identification of human NASH serum metabolic biomarkers

| Marker | Rt (min) | m/z (Da/e) | Ion | Mass Error (mDa) | Class | Common name | Fold Change | p-value |
|---|---|---|---|---|---|---|---|---|
| 5 | 3.6 | 512.2702 | [M − H]− | +2.0 | Steroid Conjugate | Sulfoglycolithocholate | 1.32 | 0.039 |
| 6 | 3.0 | 567.3102 | [M − H]− | −0.1 | Steroid Conjugate | Hyodeoxycholate-6-O-glucuronide | 1.75 | 0.003 |
| 7 | 5.3 | 463.3400 | [M − H]− | −2.3 | Bile Acid | Trihydroxycoprostanoic acid | 1.11 | 0.046 |
| 8 | 5.2 | 483.3670 | ND | ND | ND | ND | 1.33 | 0.052 |
| 9 | 6.0 | 467.3728 | [M − H]− | ND | ND | ND | 1.33 | 0.005 |
| 10 | 6.1 | 467.3719 | [M − H]− | ND | ND | ND | 1.41 | 0.015 |
| 11 | 6.2 | 467.3720 | [M − H]− | ND | ND | ND | 1.33 | 0.043 |

Peaks are listed for which there is significant discrimination between NASH (n = 20) and steatosis (11 = 54) samples [Wilcoxon rank sum (Mann Whitney) test p-values < 0.05]. Rt (min), chromatographic retention time: m/z (Da/e) [m is the neutral molecular mass value, e is the elemental charge], mass-to-charge ratio of ion detected; Ion. most intense species observed; Mass Error (mDa), difference between measured and calculated molecular mass values, calculated with respect to the identified metabolite elemental composition; Class, metabolite chemical class [putative metabolite identification was performed by accurate mass database searching and fragment ion analysis (see supplementary information), corresponding to the third level of structural assignment proposed within the Metabolomics Standards Initiative 40: "Based upon characteristic physiochemical properties of a chemical class of compounds, or by spectral similarity to known compounds of a chemical class."]; Common name, lipid nomenclature follows the LIPID MAPS convention Example 3

Metabolic Profiling of Plasma Samples Taken from Obese Patients with a Histological Diagnosis of Steatosis or NASH.

Figure 3:
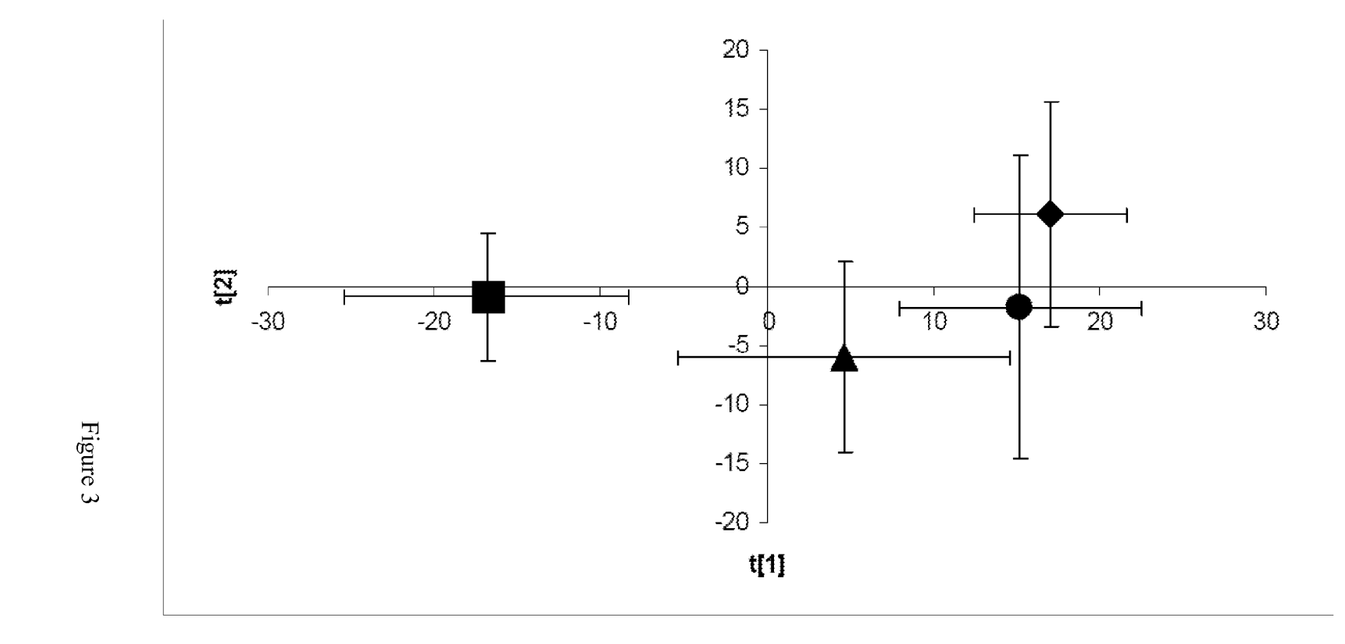
FIG. 3. Mean (±1 standard error) scores after PCA of the UPLC®-MS plasma metabolic profiling data obtained from different groups of NAFLD patients: Steatosis grade 1 (n=6), diamond; Steatosis grade 2 (n=7), circle; Steatosis grade 3 (n=3), triangle; NASH (n=14), square. Significant differences between the steatosis and NASH samples are observed as well as a clear trajectory of the different grades of steatosis along the first principal component—less severe NAFLD patients have higher, positive scores.

To determine if the metabolic profile trends observed in serum also hold for plasma, a third set of samples was analyzed, corresponding to plasma taken from 30 NAFLD patients: 16 steatosis and 14 NASH (Table 3). This set of samples was important since, in contrast to the situation in the serum samples, there was no significant difference in BMI between the plasma steatosis and NASH samples. The PCA scores plot corresponding to the plasma samples (FIG. 3) reveals very similar trends to those observed in serum; i.e. a quite clear NAFLD metabolic trajectory along the first principal component is observed.

TABLE 3

Clinical details of the patients used for the plasma sample study.

| Group | Female | Male | Age (years) | BMI (kg/m$^2$) |
|---|---|---|---|---|
| Steatosis grade 1 | 6 | 0 | 52.2 ± 2.4 | 37.3 ± 1.2 |
| Steatosis grade 2 | 5 | 2 | 46.3 ± 2.7 | 37.6 ± 3.1 |
| Steatosis grade 3 | 2 | 1 | 50.0 ± 3.5 | 42.3 ± 3.2 |
| NASH | 13 | 1 | 41.0 ± 2.5 | 37.1 ± 1.6 |

Diagnosis of steatosis and NASH was established histologically. Values are given as mean ± 1 standard error of the mean.

Example 4

Identification of NASH Serum Metabolic Biomarkers.

Having established (FIGS. 1, 2 and 3) that the metabolic profiles recorded by UPLC®-MS were correlated with NAFLD progression, the proceeding analysis was focused towards the identification of metabolic biomarkers expressing the difference between the samples taken from steatosis (regardless of grade) and NASH patients. This was achieved by OPLS-DA modeling of the data as detailed in the data processing section, whereby predictive variance related to steatosis-NASH differences is concentrated into a single component. The model resulted in one predictive and two orthogonal (1+2) components, with an encouraging cross-validated predictive ability $Q^2$=0.72. The loading profile associated with the predictive component was filtered according to steatosis-NASH discrimination power—assessed by the fold change and Wilcoxon rank sum (Mann Whitney) test p-values—and concordance with the behavior of the candidate biomarkers in the plasma samples. Following this procedure, eleven metabolites were obtained with relative ion abundances significantly different in serum samples taken from NASH patients, as compared with samples taken from individuals with steatosis (Table 2). Identification of these putative metabolite biomarkers using accurate molecular mass online database searching and fragment ion analysis (see experimental procedures and supplementary information) revealed three plasmalogens, one sphingomyelin, two steroid conjugates, one bile acid, and four molecules that could not be identified at present.

Example 5

Predictive Value of the NASH Biomarkers.

The soft independent modeling of class analogy (SIMCA) approach (Eriksson L, et al. (2006) in Multi- and Megavariate Data Analysis, Umetrics, Sweden) was used to classify the blind samples (n=10) into either steatosis or NASH groups, based on relative ion intensities corresponding to the 11 putative biomarkers. Patients in the external blind diagnosis group of samples were similar in age, BMI, AST, ALT and glucose to the group of NAFLD patients included in the OPLS-DA analysis. Local PCA models were computed for the steatosis and NASH samples and membership probability lists generated for the external blind set, based on the normalized distances of the blind samples to the local models (Table 4). Although not necessarily providing optimum class separation, this method deals reasonably well with high intra-class variation, an important factor according to the results obtained in this work, where significant metabolic differences between the 51, S2 and S3 grades of steatosis are observed. The results of this analysis show that 9/10 of the blind samples are correctly assigned; albeit patient 4 with a very small difference between the steatosis (0.997) and NASH (0.989) model membership probabilities. Patient 3 (steatosis grade 2) was incorrectly classified as NASH Although complementary clinical data is clearly necessary in order to arrive at a robust diagnosis, it is encouraging to find that in the absence of such information (age, BMI, transaminases, glucose, etc.) the metabolic data alone is sufficient to obtain a correct diagnosis for 9/10 of the patients.

TABLE 4

Predictive value of NASH metabolic biomarkers

| Patient | Histological diagnosis | NASH model Probability | Steatosis model Probability | Metabolomics diagnosis |
|---|---|---|---|---|
| 1 | Steatosis 1 | 0.451 | 0.912 | Steatosis |
| 2 | Steatosis 1 | *0.043* | 0.137 | Steatosis |
| 3 | Steatosis 2 | 0.726 | 0.115 | NASH |
| 4 | Steatosis 3 | 0.989 | 0.997 | Steatosis |
| 5 | Steatosis 3 | 0.093 | 0.441 | Steatosis |
| 6 | Steatosis 3 | 0.054 | 0.912 | Steatosis |
| 7 | NASH | 0.775 | 0.288 | NASH |
| 8 | NASH | 0.113 | *1.61 × 10$^{-5}$* | NASH |
| 9 | NASH | 0.717 | 0.466 | NASH |
| 10 | NASH | 0.727 | *0.018* | NASH |

To assess the diagnostic value of the NASH metabolic biomarkers, local PCA models were computed for the steatosis and NASH samples and classification lists generated for an external blind set of 10 serum samples. The metabolomics diagnosis was determined by the highest membership probability of belonging to either the steatosis or NASH models; membership probability values > 0.05 (95% confidence interval) are shown in bold type, whilst smaller confidence interval probabilities are shown in italics.

The invention claimed is:

1. A method for the differential diagnosis of the type of non-alcoholic fatty liver disease (NAFLD) in a patient comprising determining in a biological sample of said patient the level(s) of one or more of the metabolic markers defined in table 2 and comparing the levels of said markers with the levels of the same markers in a non-alcoholic steatohepatitis (NASH)-positive sample and/or in a steatosis positive sample, wherein
   (i) the patient is diagnosed as having NASH when the levels of one or more of the metabolic marker or markers at positions 1 to 3 and/or 5 to 11 in table 2 is/are increased with respect to the level of the same metabolic markers in a steatosis-positive sample and/or when the levels of the metabolic marker at position 4 defined in table 2 is decreased with respect to the level of the same metabolic markers in a steatosis-positive sample and/or
   (ii) the patient is diagnosed as having steatosis when the levels of one or more of the metabolic marker or markers in positions 1 to 3 and/or 5 to 11 defined in table 2 are decreased with respect to the level of the same metabolic markers in a NASH-positive sample and/or when the levels of the metabolic marker in position 4 in table 2 is increased with respect to the level of the same metabolic markers in a NASH-positive sample,
   wherein the determination of the level of the one or more biological markers is carried out by tandem mass spectrometry (MS) and wherein the biological sample is fractionated by liquid chromatography prior to the determination of the levels of the metabolic marker or markers.

2. The method according to claim 1 wherein the biological sample is serum.

3. The method according to claim 1 which comprises analyzing the levels of at least two, at least three, at least four, at least five, at least six, at least seven, at least eight, at least nine, at least ten or all eleven of the markers selected from table 2.

4. A The method according to claim 3 wherein the markers analyzed are markers 1 to 7 of table 2.

* * * * *